United States Patent
Turner et al.

(10) Patent No.: US 12,310,542 B2
(45) Date of Patent: May 27, 2025

(54) HAND CLEANSING AND MONITORING DEVICE

(71) Applicants: John Turner, St. Albans (GB); Kathryn Robinson, St. Albans (GB)

(72) Inventors: John Turner, St. Albans (GB); Kathryn Robinson, St. Albans (GB)

(*) Notice: Subject to any disclaimer, the term of this patent is extended or adjusted under 35 U.S.C. 154(b) by 32 days.

(21) Appl. No.: 17/798,163

(22) PCT Filed: Feb. 5, 2021

(86) PCT No.: PCT/EP2021/052748
§ 371 (c)(1),
(2) Date: Aug. 8, 2022

(87) PCT Pub. No.: WO2021/156408
PCT Pub. Date: Aug. 12, 2021

(65) Prior Publication Data
US 2023/0172401 A1    Jun. 8, 2023

(30) Foreign Application Priority Data
Feb. 6, 2020  (GB) .................................. 2001673

(51) Int. Cl.
*A47K 5/12* (2006.01)
*A61L 2/28* (2006.01)

(52) U.S. Cl.
CPC ............. *A47K 5/1217* (2013.01); *A61L 2/28* (2013.01)

(58) Field of Classification Search
CPC .......... A47K 5/1217; A47K 5/06; A47K 5/12; A61L 2/28; G08B 21/245
See application file for complete search history.

(56) References Cited

U.S. PATENT DOCUMENTS

| | | | |
|---|---|---|---|
| 4,938,384 A * | 7/1990 | Pilolla | A47K 5/1217 250/221 |
| 6,524,390 B1 | 2/2003 | Jones | |
| 8,795,697 B2 * | 8/2014 | Brown | A61Q 17/005 424/404 |
| 10,529,219 B2 | 1/2020 | Herdt | |
| 2007/0290865 A1 | 12/2007 | Lynn et al. | |
| 2010/0134296 A1 | 6/2010 | Hwang | |

(Continued)

FOREIGN PATENT DOCUMENTS

GB    2452189 B    7/2009
WO    2003/083033 A2    10/2003
(Continued)

OTHER PUBLICATIONS

International Search Report and Written Opinion, Application No. PCT/EP2021/052748 mailed May 3, 2021.
(Continued)

*Primary Examiner* — Donnell A Long
(74) *Attorney, Agent, or Firm* — The Dobrusin Law Firm, P.C.; Daniela M. Thompson-Walters

(57) ABSTRACT

A non-contact unitary device for hand cleansing and monitoring hand hygiene comprises means for delivery of hand cleansing material containing a light activatable marker and a space for the placement of hands after washing and provided with means for shining light onto the hands when within the space for activation of any marker remaining on the hands after washing.

20 Claims, 4 Drawing Sheets

(56) References Cited

U.S. PATENT DOCUMENTS

2018/0030701 A1* 2/2018 Bayley .................. A47K 10/48
2019/0012898 A1  1/2019 Wittrup
2019/0046679 A1  2/2019 Stoloff
2019/0211535 A1* 7/2019 Gallob .................. E03B 11/02

FOREIGN PATENT DOCUMENTS

WO  2008/112073 A2  9/2008
WO  2019/246394 A1  12/2019

OTHER PUBLICATIONS

GB Search Report dated Jul. 29, 2021, Application No. GB2101595.3.

* cited by examiner

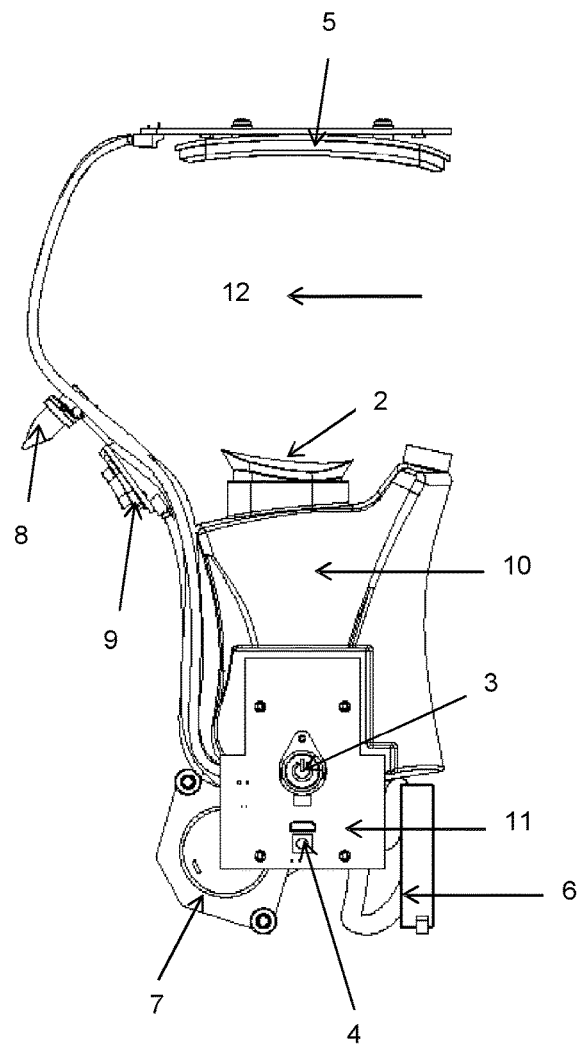
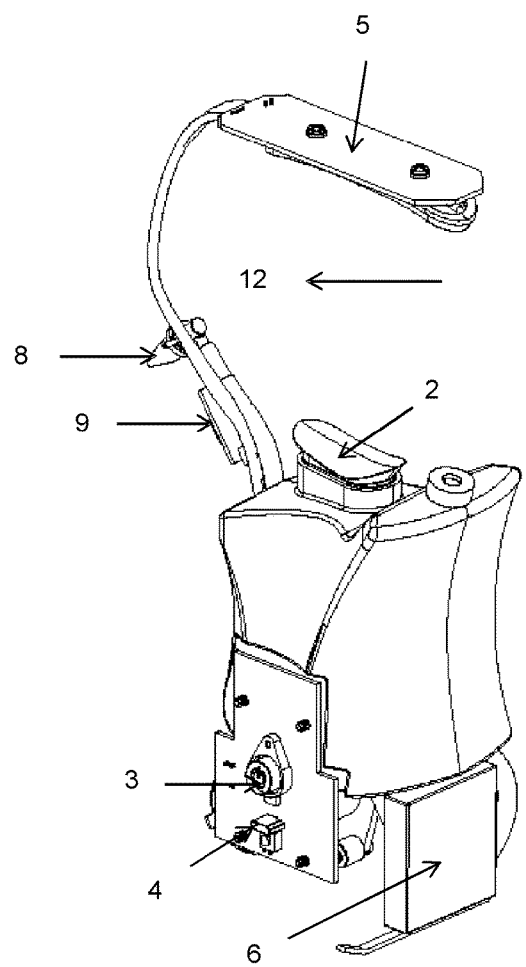
FIGURE 3
FIGURE 4

HAND CLEANSING AND MONITORING DEVICE

RELATED APPLICATIONS

This application is a National Stage of International Application No. PCT/EP2021/052748, filed Feb. 5, 2021, which claims priority to GB Patent Application No. 2001673.9, filed on Feb. 6, 2020, all of which are hereby incorporated by reference in their entirety for all purposes.

FIELD

This invention is concerned with hand cleansing and hand hygiene monitoring devices which may allow no hand contact with the device.

BACKGROUND

Given ever increasing bacterial threats to health including resistance where the armoury of antibiotics are increasingly challenged to tackle infections, it is becoming critical for personal hand hygiene to be monitored much more effectively.

The present invention provides, in embodiments, a practical and optionally portable device for hand cleansing and monitoring the effectiveness of the cleansing. Devices according to the invention find multiple applications, such as within hospitals, clinics and surgeries, food handling facilities such as factories and kitchens and many public places where hand-washing facilities are provided, amongst many others. Devices according to the invention are also applicable for use in the home, within shops and supermarkets and within offices and factories. Various designs and layouts are feasible and contemplated and devices can be constructed around their main components, and can be of any size or shape tailored to the location and means of use.

Systems for monitoring and tracking the thoroughness of hand washing/cleansing are known. For example, United Stated Patent Application publication 2010/0134296 discloses a system in which proper hygiene is determined by detecting an acceptable level of light emitted by a marker provided as a constituent of soap/disinfectant. Soap containing a marker is dispensed onto the hands and the soap dispenser sends a signal to a monitor indicating who is washing their hands. The hands are washed, rinsed, dried and then placed under a separate photometric detection system which measures the marker present on the users hands and an instruction is then provided to the user according to the amount of marker detected. The system requires at least two separate components both of which are in a fixed location; the system further requires complicated electronics for the identification of individuals, the recording of washing activities and the issuing of instructions.

United States Patent Publication 2019/0046679 relates to methods of monitoring hygiene compliance. A washing agent and a colouring agent such as an ultraviolet sensitive colour agent are applied to the skin and the presence of colour on the surface is detected over various time scales. The colouring agent is selected so that it remains on the skin for a certain period of time so that the presence of the colouring agent on the hands indicates that the hand has been properly washed.

United States Patent 10529219 relates to a system for checking if an identified individual has washed their hands after using bathroom facilities. It is not concerned with determining the efficacy of the washing and furthermore it is a permanently mounted system.

In United States Patent Publication 2007/0290865 immediately before washing the hand of a user is marked with an easily identifiable substance using an easily portable marking device. The substance is selected so that it requires good washing of the hands to remove it. The process therefore requires at least two different applications to the hands; the marking material and the washing material and furthermore requires a separate means for the detection of the marking material after washing.

SUMMARY

The present invention addresses the problems of the previous systems in that it provides a unitary device which may or may not be portable and the unitary device both delivers a washing material containing a light detectable material and additionally provides the light for the detection of the presence or otherwise of the light detectable material after washing so as to provide an indication of the sufficiency or otherwise of the washing operation.

The invention therefore provides an integrated hand cleansing and hand hygiene monitoring device comprising a housing adapted to contain internally of the housing the components of the device, power means to operate electrically controlled components of the device, a receptacle capable of containing a cleanser formulated with a light-sensitive marker, powered cleanser dispensing means, powered lighting means adapted to illuminate a hand when presented thereto with light that can identify presence of said marker on a user's hands, the device being arranged to dispense cleanser when contained in the receptacle and a hand is presented to outlet means of the dispensing means and arranged to illuminate a user's hand with such light when presented to the lighting means.

In a further embodiment the invention provides unitary device for dispensing cleanser material for hand washing and monitoring the effectiveness of the washing comprising means for dispensing cleanser material containing a light sensitive marker onto hands and means for directing light onto the hands after washing whereby the light activates any marker remaining on the hands to indicate incomplete washing.

In a preferred embodiment the component for dispensing cleanser material comprises a nozzle on the exterior of the device connected to a receptacle for the cleanser material located within the device and a pump is provided within the device for delivery of cleanser material to the nozzle which is preferably activated by a proximity sensor located on the exterior of the device close to the nozzle.

The device provides an open space for the placement of washed hands to enable light to be directed from a means for directing light onto the hands and it is preferred that the means for directing light are located above the open space so that the light is directed downwardly onto the hands when placed in the space. It is also preferred that the lights are activated by a proximity sensor which detects when hands are placed in the open space. The light may be powered by a battery which may be the same as the battery system used to power the pump.

In the preferred embodiment the light sensitive marker is sensitive to UV light particularly UVA light and the means for directing light is a UVA light source.

The use of the proximity sensors can allow cleanser delivery, washing and monitoring without any contact between the hands and the device.

In order that the invention may be illustrated, more easily appreciated and readily carried into practice by those skilled in the art, an embodiment of the invention comprising a practical and portable integrated sink side unit convenient for the user to check hand washing success when at the sink will now be described purely by way of non-limiting example with reference to the accompanying drawings, and in which:

BRIEF DESCRIPTION OF THE DRAWINGS

FIGS. 3 and 4 show an isometric view and a front elevation of the components in the FIG. 2 section view, wherein the housing has however been removed to aid clarity and understanding.

REFERRING TO THESE FIGURES

Figure 1:
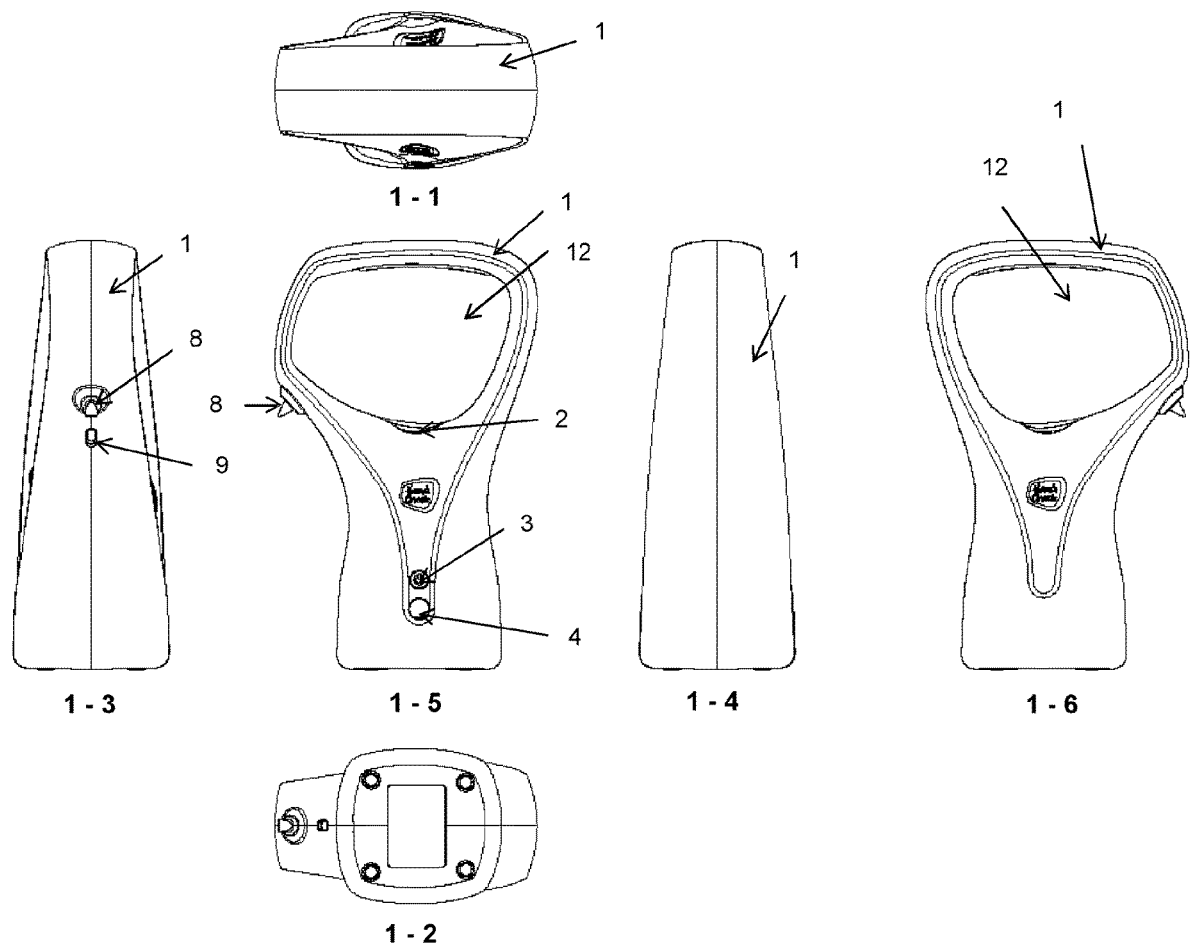
FIG. 1 shows the top (1-1); bottom (1-2); side (1-3); reverse side (1-4); front (1-5) and back (1-6) views of the external arrangement of a portable device that can be deployed sink-side in a facility where hand hygiene requires monitoring.

Key
Main body 1
Receptacle cover 2
Control Buttons 3
Charger inlet 4
Light board 5
Batteries 6
Peristaltic pump 7
Outlet Nozzle 8
Proximity Sensor 9
Cleanser Receptacle 10
Main PCB 11
Open space in housing 12

DETAILED DESCRIPTION

Figure 2:
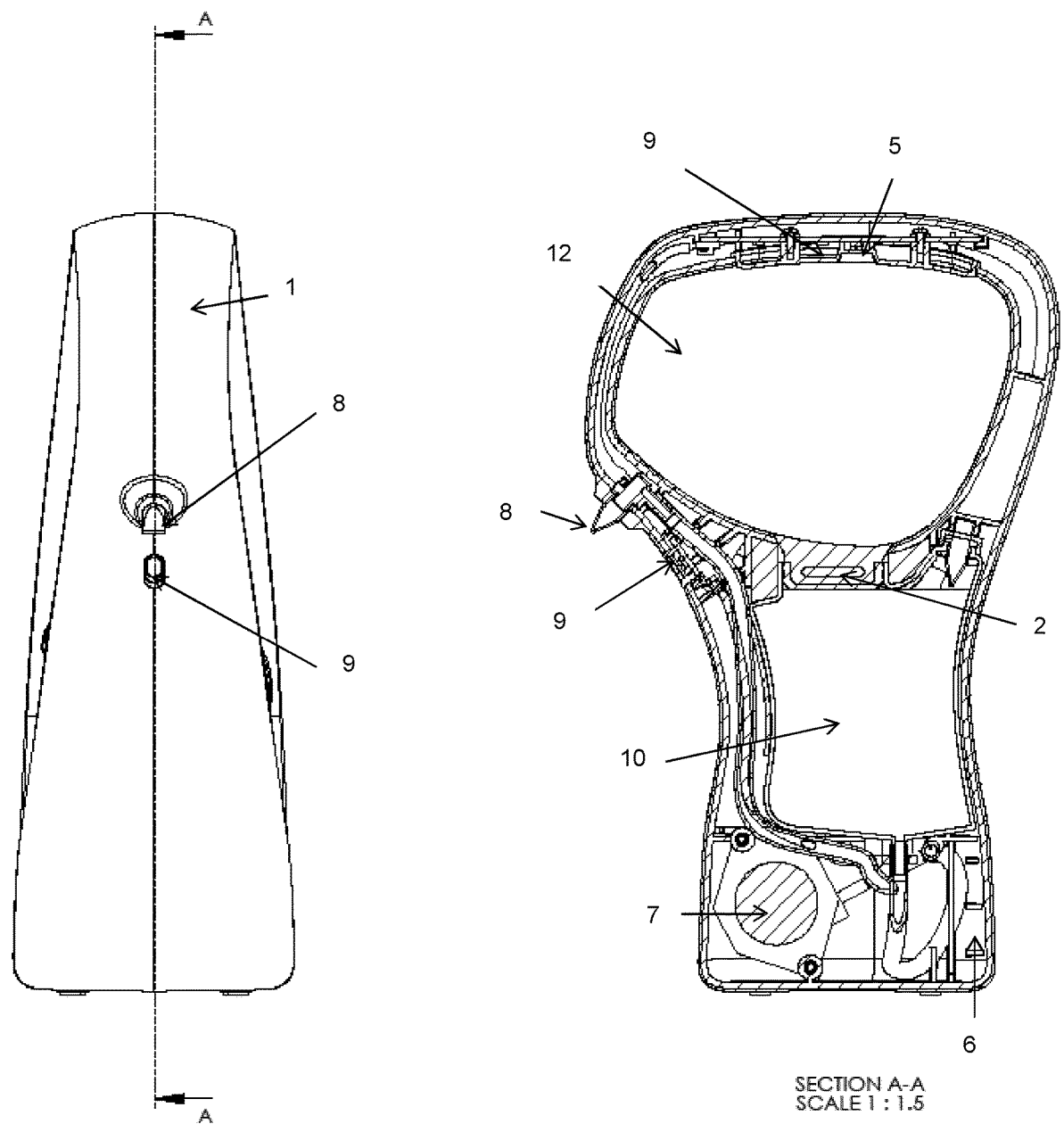
FIG. 2 shows 2 views of the FIG. 1 device, one in side elevation as in FIG. 1-3 showing a cleanser outlet nozzle and proximity sensor, the other view being a sectional view along the line A-A of the first view, and in which the powered operational components of the device can be seen.

The operation of the device will now be described with reference to FIG. 2.

In operation the user first obtains the washing material or cleanser containing the light detectable material from the dispensing nozzle 8. In a preferred embodiment this is accomplished by placing the hands adjacent to the first proximity sensor 9 at the side of the device so that an appropriate pre-measured dose of the cleanser can be dispensed onto the hands from the receptacle 10 that contains the cleansing material without the hands touching the device. In the preferred embodiment a pump 7 is provided within the device which is activated by the presence of the hands at sensor 9 to deliver a prescribed dose of the cleanser to the hands. The pump 7 may be battery powered which is preferred if the device is to be used in a portable manner. It could however be mains driven in other environments provided with a suitable safety device.

The user having received the cleanser containing the light detectable material spreads the material on the hands and then washes and rinses their hands. One or both of the hands may then be inserted into the open space of the device 12 which is provided with a light emitting array 5 positioned to direct light onto the washed hands when they are inserted into the open space. A further sensor 9 can be provided at the boundary of the open space to activate the lights when the presence of the hands in the open space is sensed which can again be accomplished without the hands touching the device. The light 5 can be powered by the same power source as is used to power the pump 7.

Once activated the light will excite any light detectable material remaining on the hands to provide a signal indicating that the washing has been insufficient and that further washing may be required.

The detailed configuration of the internals of a preferred device of this invention is shown in FIGS. 3 and 4 where the main housing body of the device has been removed. The numerals employed in FIGS. 3 and 4 relate to the same features as those in FIG. 2 which are designated by the same numeral.

The light detectable material is preferably a material that is detected by ultra violet light and the light source 5 is preferably an ultra violet light source.

The individual features of the system of the present invention will now be described in more detail.

The Cleanser Material

The cleanser material provides the user with a clear and unambiguous indication as to whether the hand washing process, carried out by a user after application of cleanser from this device directly to the hands, has or has not been carried out completely. Preferred compositions of this cleanser include a soap type component and a light-sensitive marker dye preferable a marker sensitive to ultra violet light. The cleanser composition is dispensed onto the user's hands by proximity activated sensor (although arrangements are contemplated where this may be applied manually) and the user spreads the material on the hands and washes their hands. Conveniently this may be at a sink adjacent the device. The user then inserts their hands into the hollow space element of the housing and Ultra violet lamps situated to project light onto the hand or hands within the space element are activated preferably by another proximity sensor (although arrangements are contemplated where illumination is effected more manually). Exposure to the UV light which is preferably UVA light shows the user if the hand washing process has been properly completed, as the preferred marker dye fluoresces in UV light, so absence of fluorescence indicates effective washing whereas clearly visible patches of fluorescence indicate incomplete washing and that washing will need to be repeated until there is no fluorescence.

In use the cleanser can be provided pre-mixed and in suitable containers with a practical shelf-life. Various sizes of cleanser receptacle for the device can be made available depending upon required application. Sizes for home use would typically be smaller than for commercial or industrial uses, which may warrant bulked up receptacles.

The UV Light Source

The UV light source is generally although not essentially positioned at the top of the open space of the device to direct the light in a downward direction and is connected to a power supply. The light may take different forms depending upon application and is preferably a UVA light source that is enclosed in a housing which protects the lighting and limits the risk of water and/or cleanser encroaching upon the lights and restricting their UV output.

The lighting and housing may be designed and constructed to allow examination of one hand at a time or both hands of the user. The lighting may be arranged so that it is switched on all the time or only triggered (e.g. by proximity sensor) when hands are presented to it for illumination. The UV light is intended to be safe and operate from a low voltage power supply.

To cover the eventuality that the user's hands after application of cleanser and subsequent hand washing shows that hygienic and bacteria-free wash failed, the device may incorporate (but not shown) a monitor to trigger a warning light such as a red light, with or without an audible warning to indicate that a complete wash had not been effected by the user. This would provide a warning to repeat the cleanser application and hand washing until the warning or warnings are no longer activated.

The Cleanser Dispensing Head

The dispensing head would be the point at which the cleanser is delivered, and optionally metred, onto the user's hands. A self-cleaning aperture which is preferably self-closing and non-drip, is preferably provided at the cleanser outlet to control the flow at the correct and practical rate. This could be an aperture of fixed dimensions or alternatively one that is signalled by the device to be variable. A user could adjust a button manually, or this could be achieved automatically if so signalled by an internal control of the device, for example by a level probe or other similar monitor. This component and all other components of the device in contact with the cleanser are most preferably manufactured from corrosion-resistant materials.

The action of the dispensing head could be triggered by a proximity monitor either separate from or in conjunction with the proximity monitor triggering the UV lamps as explained previously.

The structure of the dispensing head is such that easy removal of the cleanser outlet means can be achieved to facilitate maintenance.

The Pumping System

A method of transferring cleanser from its receptacle is needed. A pumping unit such as a peristatic pump is preferred and it is preferably located and fixed within the main housing of the device. The pump may be of a size suitable to match the requirements of the particular design of the device. An appropriately sized peristatic pump is preferred, although any geared, displacement or centrifugal pump capable of delivering the cleanser from the receptacle to its outlet means, would be suitable. This pump is controlled electrically from monitors, such as the aforesaid proximity sensors, but mainly the proximity trigger at the dispensing head.

Other means such as gravity or air pressure or manual pumping may be appropriate depending upon circumstance and application, to dispense cleanser via the outlet means to a user's hands.

The Cleanser Receptacle

A receptacle is needed to contain the cleanser composition and is preferably contained within the housing. The cleanser composition is typically liquid and aqueous-based although pastes and gels are contemplated in alternative embodiments. This receptacle not only provides means whereby the cleanser is contained but is preferably integrated into the inside of the main housing of the device and connected to the pump to enable delivery of the cleanser to the dispensing head. The receptacle has an aperture enabling cleanser to be added to the device. This aperture has a closure such as a removable lid.

The receptacle for cleanser is preferably transparent and visible from outside the housing of the device to enable the user to establish the level of cleanser, or alternatively if opaque it may be fitted with a monitor to indicate to the user the level of cleanser optionally with a warning light to show when more cleanser is required. Alternatively the level can be checked visually by looking into the receptacle.

Power Supply

The base of the housing of the integrated device unit of this invention preferably contains the means whereby the powered electrical components of the device are housed and also the power source and/or provides access to an external power source for example for the charging of the internal power source.

The power components can include low voltage switches and wiring/PCB boards to control the pump, dispensing head, UV light and any other monitors/proximity sensors fitted to the device.

The isolating means for the device is included in this area.

Figure 5:
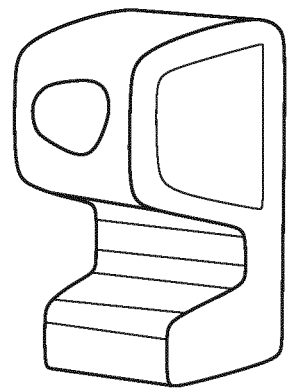
FIGS. 5 and 6 show alternate designs of the device.
Figure 6:
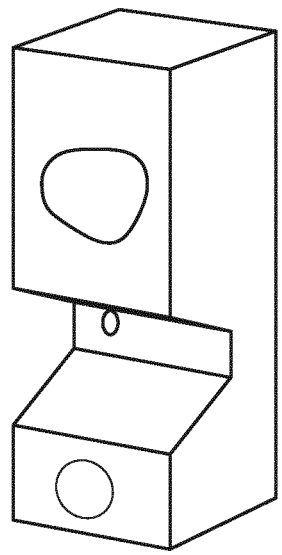

Although the device of this invention has been illustrated and described as having a particular size and shape the size and shape can be varied according to the environment in which the device is to be used. The material from which it is made may be chosen according to the use to which it is to be put. For example, the main body of a portable device would preferably be made of light weight but strong material such as thermoplastics perhaps filled with reinforcing material. An industrial device such as one for use in factories, hospitals and the like could be of stronger longer lasting material perhaps of stainless steel. The shape of the device may also be varied to provide the optimum shape for particular uses and the attached FIGS. 5 and 6 show alternate designs which operate in the same manner as described herein.

What is claimed is:

1. A unitary device for dispensing a cleanser material for hand washing and monitoring the effectiveness of the hand washing comprising:
    a) a means for dispensing the cleanser material containing a light sensitive marker onto hands;
    b) a means for directing a light onto the hands after the hand washing, wherein the light activates any of the light sensitive marker remaining on the hands to indicate the hand washing is incomplete; and
    c) an open space for placement of the hands after the hand washing to enable the light to be directed onto the hands from the means for directing the light, and wherein the means for directing the light are located above the open space so that the light is directed downwardly onto the bands when placed in the open space.

2. The unitary device according to claim 1, wherein the means for dispensing the cleanser material comprises a nozzle on an exterior of the unitary device connected to a receptacle for the cleanser material located within the unitary device.

3. The unitary device according to claim 2, wherein a pump is located within the unitary device for delivery of the cleanser material to the nozzle.

4. The unitary device according to claim 3, wherein the pump is activated by a proximity sensor located on the exterior of the unitary device close to the nozzle.

5. The unitary device according to claim 1, wherein the light is activated by a proximity sensor which detects when the hands are placed in the open space.

6. The unitary device according to claim 1, wherein the unitary device is portable.

7. The unitary device according to claim 6, wherein the unitary device includes a hand drier.

8. The unitary device according to claim 1, wherein the light sensitive marker is sensitive to UV light, and the means for directing the light is a UV light source.

9. The unitary device according to claim 1, wherein the unitary device is an integrated hand cleansing and hand hygiene monitoring device comprising:
   (a) a housing adapted to contain internally and house components of the unitary device;
   (b) a power means to operate electrically controlled components of the unitary device;
   (c) a receptacle capable of containing the cleanser material formulated with the light sensitive marker;
   (d) the means for dispensing the cleanser material, wherein the means for dispensing the cleansing material is powered;
   (e) the means for directing the light, wherein the means for directing the light is powered and adapted to illuminate the hands when presented with the light to identify a presence of the light sensitive marker; and
   wherein the unitary device is arranged to dispense the cleanser material when contained in the receptacle and the hands are presented to an outlet means of a component for dispensing the cleanser material- and arranged to illuminate the hands with the light when presented to the means for directing the light.

10. The unitary device according to claim 9, wherein the housing is a self-contained, standalone, integrated unit.

11. The unitary device according to claim 9, wherein the housing comprises the open space which is a hollow ring portion through which a hand can be inserted and withdrawn.

12. The unitary device according to claim 11, wherein the hollow ring portion comprises the means for directing the light.

13. The unitary device according to claim 9, wherein the power means is battery operated and includes a battery holder for a plurality of batteries.

14. The unitary device according to claim 9, wherein the means for dispensing the cleanser material is operated by a pump situated internally within the housing.

15. The unitary device according to claim 9, wherein the means for dispensing the cleanser material is associated with a primary proximity sensor for detecting a presence of a hand near the outlet means of the component for dispensing the cleanser material, and operable to actuate the component for dispensing the cleanser material.

16. The unitary device according to claim 15, wherein the means for directing the light is associated with a secondary proximity sensor for detecting the presence of the hand near the means for directing the light, and operable to actuate illumination of the hand.

17. The unitary device according to claim 9, wherein the means for directing the light comprises UV lamps adapted to illuminate the light sensitive marker in the cleanser material.

18. A method of identifying complete or incomplete hand washing comprising use of the unitary device according to claim 1, and gauging the level of effective hand washing by identification of any patches of the cleanser material remaining on a user's hand after washing, wherein the patches are being identified by response of the light sensitive marker in the cleanser material to illumination.

19. A device for dispensing a cleanser material for hand washing and monitoring an effectiveness of the hand washing, the device comprising:
   a) a main body forming a housing of the device, wherein the main body includes:
      i) an open space configured to receive hands therein after washing;
      ii) a receptacle within an interior of the housing configured to contain the cleanser material;
   b) a dispensing nozzle connected to the receptacle and at an exterior of the main body, wherein the dispensing nozzle is configured to dispense the cleanser material;
   c) a first proximity sensor located in proximity to the dispensing nozzle and configured to detect placement of the hands near the dispensing nozzle;
   d) a pump located within the main body which is configured to transfer the cleanser material to the dispensing nozzle upon detection of the hands by the first proximity sensor;
   e) a second proximity sensor located on the main body adjacent to the open space and configured to detect placement of the hands within the open space;
   f) a light source located on the main body and above the open space so that a light emitted from the light source is directed downwardly onto the hands when placed in the open space, wherein the light source is configured to emit the light upon detection of the hands by the second proximity sensor; and
   wherein the cleansing material contains a light sensitive marker and wherein the light emitted by the light source activates any of the light sensitive marker remaining on the hands to indicate incomplete washing.

20. The device of claim 19, wherein the device is battery operated such that the device is a portable device.

* * * * *